United States Patent
Braithwaite et al.

(10) Patent No.: US 9,873,769 B2
(45) Date of Patent: Jan. 23, 2018

(54) THIOLATED PEG-PVA HYDROGELS

(71) Applicant: CAMBRIDGE POLYMER GROUP, INC., Boston, MA (US)

(72) Inventors: Gavin Braithwaite, Cambridge, MA (US); Yuri Svirkin, Winchester, MA (US)

(73) Assignee: CAMBRIDGE POLYMER GROUP, INC., Boston, MA (US)

( * ) Notice: Subject to any disclaimer, the term of this patent is extended or adjusted under 35 U.S.C. 154(b) by 40 days.

(21) Appl. No.: 14/328,176

(22) Filed: Jul. 10, 2014

(65) Prior Publication Data

US 2016/0009872 A1 Jan. 14, 2016

(51) Int. Cl.
- *C08J 3/075* (2006.01)
- *A61K 31/795* (2006.01)
- *A61K 47/32* (2006.01)
- *A61K 31/00* (2006.01)

(52) U.S. Cl.
CPC .............. *C08J 3/075* (2013.01); *A61K 31/00* (2013.01); *A61K 31/795* (2013.01); *A61K 47/32* (2013.01); *C08J 2329/04* (2013.01)

(58) Field of Classification Search
CPC ....... A61K 31/795; A61K 47/32; C08J 3/075; C08J 2329/04
See application file for complete search history.

(56) References Cited

U.S. PATENT DOCUMENTS

| | | | |
|---|---|---|---|
| 2,443,923 A * | 6/1948 | Mortenson | C08F 8/34 525/61 |
| 4,565,854 A | 1/1986 | Sato et al. | |
| 5,981,826 A | 11/1999 | Ku et al. | |
| 6,231,605 B1 | 5/2001 | Ku | |
| 6,268,405 B1 | 7/2001 | Yao et al. | |
| 7,288,608 B2 | 10/2007 | Bowman et al. | |
| 7,745,532 B2 | 6/2010 | Ruberti et al. | |
| 7,776,352 B2 * | 8/2010 | Ruberti | A61F 2/442 424/423 |
| 8,287,595 B2 | 10/2012 | Vresilovic et al. | |
| 8,637,063 B2 * | 1/2014 | Kopesky | C08F 218/08 424/422 |
| 2002/0068087 A1 * | 6/2002 | Marchant | A61K 47/32 424/486 |
| 2004/0089533 A1 | 5/2004 | Hoagland et al. | |
| 2004/0171740 A1 * | 9/2004 | Ruberti | A61F 2/442 524/563 |
| 2010/0086678 A1 | 4/2010 | Arthur et al. | |
| 2011/0256201 A1 * | 10/2011 | Kopesky | C08F 218/08 424/422 |
| 2014/0089533 A1 * | 3/2014 | Saripalli | G06F 9/4812 710/8 |
| 2014/0277112 A1 * | 9/2014 | Mellin | A61K 47/34 606/213 |

OTHER PUBLICATIONS

Alves et al., "Poly(Vinyl Alcohol) Physical Hydrogels: New Vista on a Long Serving Biomaterial"; 2011; Macromolecular Bioscience, 11:1293-1313.*
Bernkop-Schnuerch, "Thiomers: A new generation of mucoadhesive polymers"; 2005; Advanced Drug Delivery Reviews, 57:1569-1582.*
Dong et al., "Imaging and Thermal Studies of Wheat Gluten/Poly(vinyl alcohol) and Wheat Glluten/Thiolated Poly(Vinyl alcohol) Blends"; 2008; Biomacromolecules, 9:568-573.*
Dicharry et al., "Wheat Gluten-Thiolated Poly(vinyl alcohol) Blends with Improved Mechanical Properties"; 2006; Biomacromolecules, 7:2837-2844.*
Martens et al., "Tailoring the Degradation of Hydrogels Formed from Multivinyl Poly(ethylene glycol) and Poly(vinyl alcohol) Macromers for Cartilage Tissue Engineering"; 2003; Biomacromolecules, 4(2):283-292.*
Ossipov et al., "Poly(vinyl alcohol) Cross-Linkers for in Vivo Injectable Hydrogels"; 2008; Macromolecules, 41:3971-3982.*
Stephens-Altus et al., "Development of bioactive photocrosslinkable fibrous hydrogels"; 2010; J. of Biomedical Materials Research Part A, pp. 167-176.*
Qiu et al., "A hydrogel prepared by in situ cross-linking of a thiol-containing poly(ethylene glycol)-based copolymer: a new biomaterial for protein drug delivery"; 2003; Biomaterials, 24:11-18.*
Chen et al., Versatile Synthesis of Functional Biodegradable Polymers by Combining Ring-Opening Polymerization and Postpolymerization Modification via Michael-Type Addition Reaction, 2010; Macromolecules, 43(1):201-207.*
Ossipov et al., Poly(vinyl alcohol) Cross-Linkers for in Vivo Injectable Hydrogels; 2008; Macromolecules, 41:3971-3982.*
Desroches et al., Synthesis of Biobased Polyols by Thiol-Ene Coupling from Vegetable Oils; 2011; Macromolecules; 44(8):24898-2500.*
Dong et al., Imaging and Thermal Studies of Wheat Gluten/Poly(vinyl alcohol) and Wheat Gluten/Thiolated Poly(vinyl alcohol) Blends; 2008, Biomacromolecules, 9:568-573.*
Alves et al., Poly(Vinyl Alcohol) Physical Hydrogels: New Vista on a Long Serving Biomaterial; 2011; Macromolecular Bioscience, 11:1293-1313.*
Bernkop-Schnuerch, Thiomers: A new generation of mucoadhesive polymers; 2005; Advanced Drug Delivery Reviews, 57:1569-1582.*
Dicharry et al., Wheat Gluten-Thiolated Poly(vinyl alcohol) Blends with Improved Mechanical Properties; 2006; Biomacromolecules, 7:2873-2844.*
Martens et al., Tailoring the Degradation of Hydrogels Formed from Multivinyl Poly(ethylene glycol) and Poly (vinyl alcohol) Macromers for Cartilage Tissue Engineering; 2003; Biomacromolecules, 4(2):283-292.*

(Continued)

*Primary Examiner* — Mina Haghighatian
*Assistant Examiner* — Erin Hirt
(74) *Attorney, Agent, or Firm* — Grossman, Tucker, Perreault & Pfleger, PLLC

(57) ABSTRACT

A method of forming thiolated poly(vinyl alcohol) hydrogels including reacting, in the presence of an acid, compounds containing a thiol functional group and a hydroxyl reactive group with one or more hydroxyl groups of poly (vinyl alcohol) via said hydroxyl reactive group, thereby forming thiolated poly(vinyl alcohol). The method further including reacting the thiol functional group of said compounds with a thiol reactive group of a crosslinker, thereby forming a hydrogel.

32 Claims, 10 Drawing Sheets

(56) References Cited

OTHER PUBLICATIONS

Stephens-Altus et al., Development of bioactive photocrosslinkable fibrous hydrogels, 2010; J. of Biomedical Materials Research Part A, pp. 167-176.*

Qiu et al., A hydrogel prepared by in situ cross-linking of a thiol-containing poly(ethyelene glycol)-based copolymer: a new biomaterial for protein drug delivery; 2003; Biomaterials 24:11-18.*

Chen et al., "Versatile Synthesis of Functional Biodegradable Polymers by Combining Ring-Opening Polymerizaton and Postpolymerization Modificaton via Michael-Type Addition Reaction", Marcromolecules, Jan. 12, 2010, vol. 43(1), pp. 201-207.

Desroches et al., "Synthesis of Biobased Polyois by Thiol-Ene Coupling from Vegetable Oils", Macromolecules, Apr. 26, 2011, vol. 44(8), pp. 2489-2500.

International Search Report and Written Opinion from corresponding PCT Appln. No. PCT/US15/39492, dated Oct. 2015.

Elbert et al., "Protein delivery from materials formed by self-selective conjugate addition reactions", Journal of Controlled Release, Release 76, 2001, pp. 11-25, Switzerland.

Alves et al., "Poly(Vinyl Alcohol) Physical Hydrogels: New Vista on a Long Serving Biomaterial", Macromolecular Bioscience, vol. 11, pp. 1293-1313, 2011, Germany.

Bernkop-Schnuerch, "Thiomers: A new generation of mucoadhesive polymers", Advanced Drug Delivery Reviews, vol. 57, pp. 1569-1582, 2005, Austria.

Dicharry et al., "Wheat Gluten—Thiolated Poly(vinyl alcohol) Blends with Improved Mechanical Properties", Biomacromolecules, vol. 7, pp. 2837-2844, 2006, Storrs, Connecticut.

Dicharry et al., "Imaging and Thermal Studies of Wheat Gluten/Poly(vinyl alcohol) and Wheat Gluten/Thiolated Poly (vinyl alcohol) Blends", Biomacromolecules, vol. 9, pp. 568-573, 2008, Storrs, Connecticut.

Hiemstra, In Situ Forming Biodegradable Hydrogels and Their Application for Protein Delivery, pp. 1-253, 1978, Netherlands.

Lundberg et al., "Poly(ethylene glycol)-Based Thiol-ene Hydrogel Coatings—Curing Chemistry, Aqueous Stability, and Potential Marine Antifouling Applications", ACS Applied Materials & Interfaces, vol. 8, pp. 903-912, 2010, Sweden.

Martens et al., "Tailoring the Degradation of Hydrogels Formed from Multivinyl Poly(ethylene glycol) and Poly(vinyl alcohol) Macromers for Cartilage Tissue Engineering", Biomacromolecules, vol. 4 (2), pp. 283-292, 2003, Washington D.C.

Ossipov et al. "Poly(vinyl alcohol) Cross-Linkers for in Vivo Injectable Hydrogels" Macromolecules, vol. 41, pp. 3971-3982, 2008, Sweden.

Reyes et al. "A Modified Chondroitin Sulfate Aldehyde Adhesive for Sealing Corneal Incisions" Investigative Ophthalmology & Visual Science, vol. 46, (4), pp. 1247-1250, 2005, Baltimore, MD.

Roberts, "New In Situ Crosslinking Chemistries for Hydrogelation", PhD Dissertation, University of Utah, pp. 1-149, 2008.

Slaughter et al., "Hydrogels in Regenerative Medicine", Advanced Materials, vol. 21, pp. 3307-3329, 2009, Germany.

Stephens-Altus et al., "Development of bioactive photocrosslinkable fibrous hydrogels", Journal of Biomedical Materials Research Part A, pp. 167-176, 2010, Texas.

Tan et al., "Injectable, Biodegradeable Hydrogels for Tissue Engineering Applications", Materials, vol. 3, pp. 1746-1767, 2010, Pennsylvania.

Totani et al., "Immobilization of urokinase on the islet surface by amphiphilic poly(vinyl alcohol) that carries alkyl side chains", Biomaterials Journal, vol. 29, pp. 2878-2883, 2008, Japan.

* cited by examiner

THIOLATED PEG-PVA HYDROGELS

FIELD OF INVENTION

The present disclosure is directed to hydrogels that are prepared in situ through cross-linking thiolated poly(vinyl alcohol) (TPVA) and, in particular embodiments, crosslinking thiolated poly(vinyl alcohol) with poly(ethylene glycol) (PEG) containing thiol-reactive group.

BACKGROUND

Hydrogels of poly(vinyl alcohol) (PVA) and poly(ethylene glycol) (PEG) are used in a variety of biomedical and pharmaceutical applications including tissue scaffolds, cartilage repair, and drug delivery. Various methods have been proposed for making such hydrogels. For example, some methods for hydrogel preparation from poly(vinyl alcohol) (PVA) and poly(ethylene glycol) (PEG) are based on the incorporation of vinyl functionalities into macromers with consequent photopolymerization that requires the use of photoinitiators and a UV source. In other cases, PVA is end-capped with thiol groups and cross-linked with methacryloyl-substituted PVA. However, many of these systems require the use of initiators, (which may be toxic), UV radiation, organic solvents, and temperatures outside of those tolerable in physiological conditions.

Accordingly, room still remains for improvement in systems that can be injected and form hydrogels in situ under physiological conditions without toxic initiators, UV radiation, organic solvents or elevated temperatures. In addition, hydrogel systems that are degradable and biocompatible are desired that form degradation products that pass through the kidneys. Furthermore, it is desirable to provide a polymer system that is capable of both crosslinking for the purpose of hydrogel formation and mucoadhesion.

SUMMARY

An aspect of the present disclosure relates to a method of forming thiolated poly(vinyl alcohol) hydrogels. The method includes reacting, in the presence of an acid, compounds containing a thiol functional group and a hydroxyl reactive group with one or more hydroxyl groups of poly(vinyl alcohol) via said hydroxyl reactive group, thereby forming thiolated poly(vinyl alcohol). The method further including reacting the thiol functional group of said compounds with a thiol reactive group of a crosslinker, thereby forming a hydrogel.

BRIEF DESCRIPTION OF THE FIGURES

The above-mentioned and other features of this disclosure, and the manner of attaining them, may become more apparent and better understood by reference to the following description of embodiments described herein taken in conjunction with the accompanying drawings, wherein.

DESCRIPTION

Figure 1A:
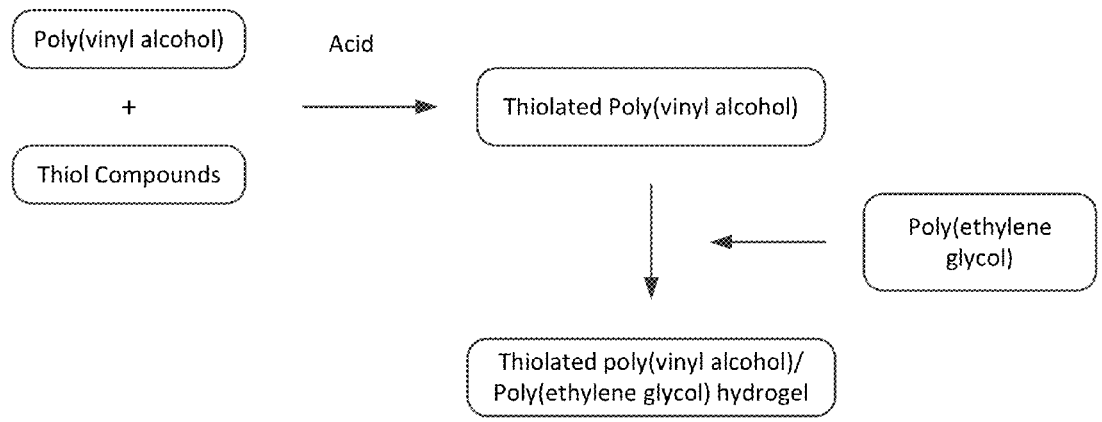
FIG. 1a illustrates a flow diagram of an embodiment of forming the thiolated poly(vinyl alcohol) and poly(ethylene glycol) hydrogels.

The present disclosure is directed to hydrogels that are prepared by a cross-linking reaction of thiolated poly(vinyl alcohol) (TPVA) with poly(ethylene glycol) (PEG) containing thiol-reactive groups. Thiol groups are incorporated into poly(vinyl alcohol) (PVA) by coupling to the hydroxyl groups of the poly(vinyl alcohol) thiol functionalities or protected thiol functionalities with subsequent deprotection. Commonly available poly(ethylene glycol) polymers contain end group functionalities reactive towards the thiol groups (acrylates, methacrylates, maleimide, N-hydroxysuccinimide, etc). In particular embodiments, the hydrogels are formed in situ upon mixing due to the cross-linking reaction of the thiolated poly(vinyl alcohol) (TPVA) and polyethylene glycol (PEG) containing thiol-reactive groups in aqueous solution.

Crosslinking of the thiolated poly(vinyl alcohol) and the poly(ethylene glycol) including thiol reactive groups occurs without heat release and formation of by-products and does not require use of toxic initiators or a UV source. Nor is a freeze-thaw process necessarily employed as is commonly used to form poly(vinyl alcohol) hydrogels. Residual unreacted products include end-functional poly(ethylene glycol) and modified thiolated poly(vinyl alcohol), as no initiator or toxic crosslinker is required. Further, in particular embodiments, such as where poly(ethylene glycol) is poly(ethylene glycol) diacrylate (PEGDA), reaction of the poly(ethylene glycol) and thiolated poly(vinyl alcohol) is an addition reaction and doesn't produce unwanted by-products.

In embodiments, the thiolated poly(vinyl alcohol) and poly(ethylene glycol) cross-linking reactions proceed at temperatures in the range of 0° C. to 95° C., including all values and ranges therein, such as 20° C. to 45° C. In addition, crosslinking may be largely unaffected by pH or other solutes. In particular embodiments, crosslinking occurs under physiological conditions, wherein physiological conditions may be understood as conditions of the internal or external milieu that may occur in nature for an organism and include, for example, temperatures in the range of 20° C. to 40° C., a pH in the range of 6 to 8, and glucose concentrations in the range of 1 mM to 20 mM.

The hydrogels are employed in a variety of applications, and particularly biologically based applications. Examples of such applications include cartilage repair (such as the injection of the hydrogels into defects or the manufacture of the hydrogels for implantation), cell or drug carriers, high light transmission carriers for sensing molecules, active drugs, or active ingredients (e.g. glucose sensors, detectors, coatings on surgical instruments or optical analysis probes (in vivo or industrially)), temporary tissue bulking, hydrogels with additional actives chemically attached to the hydrogel backbone, molding compounds for tissue mimics or phantoms, as well as coating material for medical devices. Accordingly, in embodiments, the thiolated poly(vinyl alcohol) and poly(ethylene glycol) are delivered as individual components and combined in situ or combined within a few minutes prior to delivery. In other embodiments, the thiolated poly(vinyl alcohol) and poly(ethylene glycol) are combined and formed in advance of delivery into items, such as a sheet, a tube, or a scaffold. The hydrogels may also have value as heavy metal chelating agents whereby the thiol groups associate with heavy metals, such as zinc, mercury, lead or cadmium in the medium. The hydrogel would thus act as a heavy metal filter in some applications. In further embodiments, the hydrogels bind to groups present in tissue, including possibly mucins, other thiol groups or any other thiol reactive group, such as cysteine residues on proteins or glutathione. The hydrogels may also bind to heavy metals in the blood stream, possibly providing a method chelating these toxic elements out of the system.

Figure 1B:
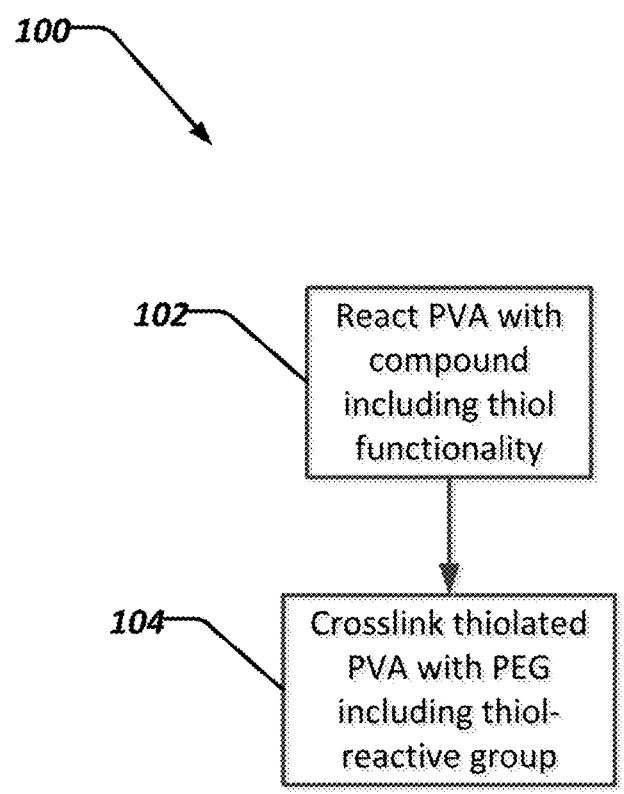
FIG. 1b illustrates a schematic diagram of a method of forming the thiolated poly(vinyl alcohol) and poly(ethylene glycol) hydrogels.

FIG. 1a illustrates a flow diagram of an embodiment of forming thiolated poly(vinyl alcohol) and poly(ethylene glycol) hydrogels and FIG. 1b illustrates a method 100 of forming thiolated poly(vinyl alcohol) and poly(ethylene glycol) hydrogels as illustrated in the flow diagram of FIG. 1a. In this embodiment, the method begins with forming the thiolated poly(vinyl alcohol) by reacting compounds containing hydroxyl reactive groups and thiol groups, or protected thiol groups (with subsequent de-protection), to the hydroxyl groups of the poly(vinyl alcohol) in the presence of an acid. Reaction of the thiol containing compounds is accomplished through, for example, esterification, see 102 of FIG. 1b. Other molecules that may be suitable are glutathione, mercaptoethanol and dithiothreitol.

Turning to the poly(vinyl alcohol), the poly(vinyl alcohol) is hydrolyzed or partially hydrolyzed to 75% or more, including all values and ranges from 75% to 99.9%, including 75%, 80%, 85%, 90%, 95%, 96%, 97%, 98%, 99%, etc. In addition, the molecular weight (Mw) of the poly(vinyl alcohol) is in the range of 2 kDa to 2,000,000 kDa, including all values and ranges therein, and preferably 2 kDa to 1,000,000 kDa, and more preferably 2 kDa to 200 kDa, and more preferably 30 kDa to 50 kDa, etc. The poly(vinyl alcohol) is provided in a solution, dissolved in water or other solvents (including, but not limited to, dimethyl sulfoxide (DMSO) or dimethylformamide (DMF)) at any viable concentration and preferably at a concentration in the range of 0.0001 wt % to 50 wt %, including all values and increments therein.

A range of thiol containing functional groups can be reacted with to the poly(vinyl alcohol) and are added to the poly(vinyl alcohol) solution. In embodiments, compounds include the thiol functionality and at least one hydroxyl-reactive group, such as, for example carboxyl groups, represented by the following formula of Equation 1.

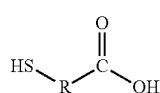

Eq. 1)

wherein R may include an alkane, iso-alkane, unsaturated ether, or ester group, and R includes from 1 to 20 carbons.

In further embodiments, it is contemplated that the hydroxyl-reactive groups (i.e., the carboxyl group) may include or be substituted with other acids, acyl halogenates, acid anhydrides esters, etc. having from 1 to 10 carbon atoms, represented by formula of the Equation 2.

Eq. 2)

In particular embodiments, the thiol containing functional groups include 3-mercaptopropionic acid and thiolation of the poly(vinyl alcohol) occurs through esterification forming ester bonds.

Figure 2:
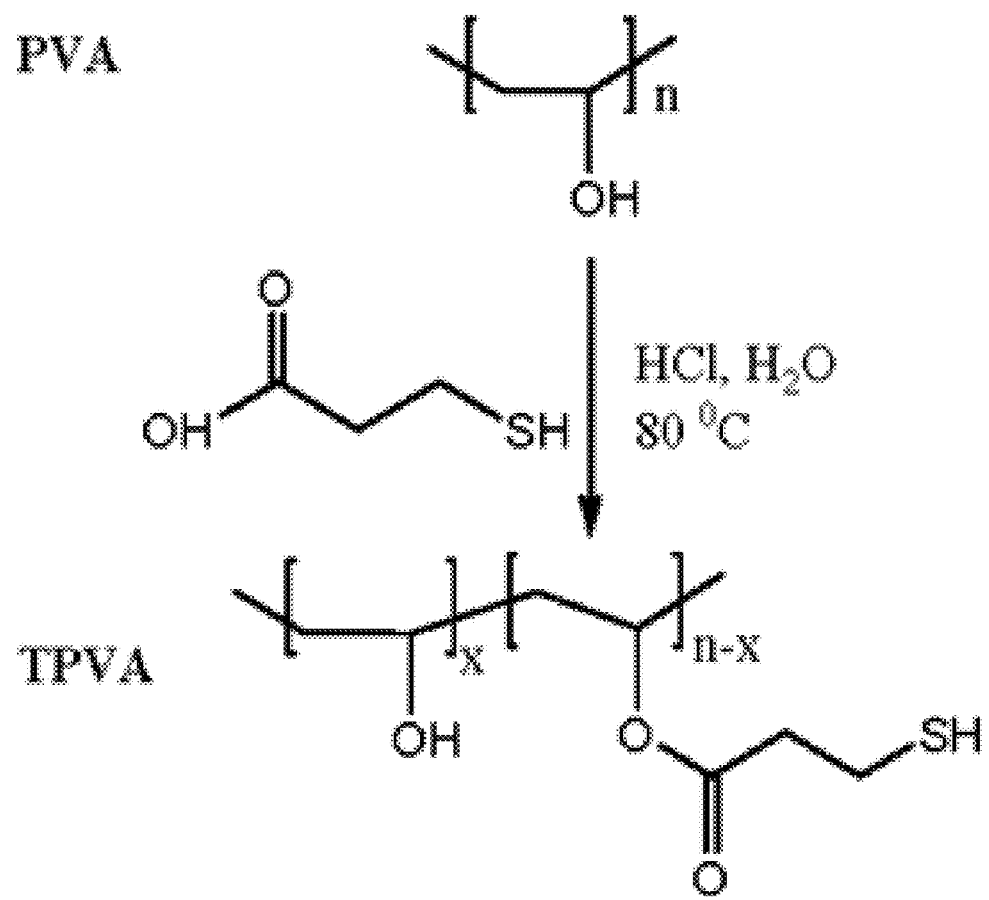
FIG. 2 illustrates an example of a reaction scheme for the esterification reaction of a thiol containing compound including at least one hydroxyl-reactive group and poly(vinyl alcohol)

As noted above, the thiolation of the poly(vinyl alcohol) occurs in the presence of an acid, such as hydrochloric acid, sulfuric acid or phosphoric acid. In addition, thiolation occurs at moderately elevated temperatures, such as in the range of 40° C. to 95° C., including all values and ranges therein, preferably at 60° C. to 85° C. and, more preferably at 75° C. to 85° C. FIG. 2 illustrates an example of a reaction scheme for an esterification reaction of 3-mercaptopropionic acid with the poly(vinyl alcohol), wherein the reaction is performed in the presence of HCl, at 80° C.

In embodiments, the thiolated poly(vinyl alcohol) includes compositions having the general formula set forth in Equation 3 below.

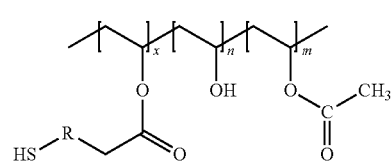

Eq. 3)

wherein R includes 1 to 20 carbons and may be an alkane, isoalkane, saturated ether or ester, and the individual units are randomly distributed along the length of the poly(vinyl alcohol) chain. X is in the range of 0.1-10%, n is in the range of 80-99.9%, indicating the level of hydrolysis of the poly(vinyl alcohol) polymer and allowing for water solubility of the polymer and m, the amount of non-hydrolyzed acetate groups, is in the range 0.1-20%.

In embodiments, the degree of modification of the poly (vinyl alcohol) can be regulated by the number of esterified hydroxyl groups of the polyvinyl alcohol. Thiol compounds may be present at a ratio of 0.1 mmol per mmol to 10.0 mmol per mmol of poly(vinyl alcohol), including all values and ranges therein. Furthermore, the degree of modification of the poly(vinyl alcohol) can be regulated by the reaction temperature and reaction time. In embodiments, the reaction temperature may be in the range of 40° C. to 95° C. as discussed above, and reaction time may be in the range of 5 hours to 48 hours, including all values and ranges therein. However, cooler reaction temperatures may be utilized as well, such as in the range of 20° C. up to 40° C. A condition of modification is to not exceed aqueous solubility limit.

As illustrated above, thiol group incorporation is accomplished by a one-step reaction, not requiring modification of poly(vinyl alcohol)'s hydroxyl groups or protection/de-protection chemistry of 3-mercaptopropionic acid. In addition, or alternatively, it is contemplated that amino acids including thiol functionality are coupled through poly(vinyl alcohol)'s hydroxyl groups via protection/de-protection chemistry. An example of an amino acid containing thiol functionalities is cysteine and "direct" poly(vinyl alcohol) esterification with L-cysteine, similar to esterification with 3-mercaptopropionic acid, is contemplated. Likewise, it may be possible to couple other molecules such as coenzyme A and coenzyme M. Any suitable thiol and hydroxyl reactive group containing molecules may be used in this process, such as glutathione, mercaptoethanol and dithiothreitol. The thiol-groups' affinity to heavy metals may also have value as a chelating agent removing heavy metals from water supplies or other contaminated media. This chelating construct could be in the form of a hydrogel-based filter, or as hydrogel microparticles. In addition the thiol group can react with other thiol groups, such as those in cysteine to form disulphide bonds. Thus the thiolated PVA will bind to the cysteine group in collagen and other cysteine containing proteins.

Referring again to FIGS. 1a and 1b, hydrogels are then formed 104 in situ by cross-linking the thiolated poly(vinyl alcohol) (TPVA) with poly(ethylene glycol) (PEG) endcapped with thiol-reactive groups. The poly(ethylene glycol) endcapped with thiol-reactive groups may be linear, branched, dendrimers or multi-armed. The thiol reactive groups may include, for example, acrylates, methacrylates, maleimide, haloacetyl, pyridyldithiol N-hydroxysuccinimide, etc.

A general formula of the poly(ethylene glycol) endcapped with thiol-reactive groups is set forth in equation 5 below, although as noted above it is understood that the ethylene glycol group may be multi-armed or a dendrimer.

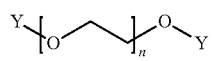

Eq. 5)

wherein, each Y individually selected from a thiol reactive end group including the above mentioned end groups and n is in the range of 200 to 20,000. In particular embodiments, Y is an acrylate as represented by the formula set forth in Eq. 6 below.

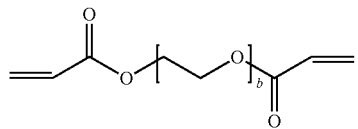

Eq. 6)

wherein b is in the range of 200 to 20,000.

Alternatively or additionally to the linear embodiments of equations 5 and 6 depicted above, the poly(ethylene glycol) may be a dendrimer. For example, the poly(ethylene glycol) may be a 4 to 32 hydroxyl dendron. In further alternative or additional embodiments, the poly(ethylene glycol) may be multi-armed. In such embodiments, the poly(ethylene glycol) may be, for example, a 4, 6 or 8 arm and hydroxy-terminated.

Figure 3:
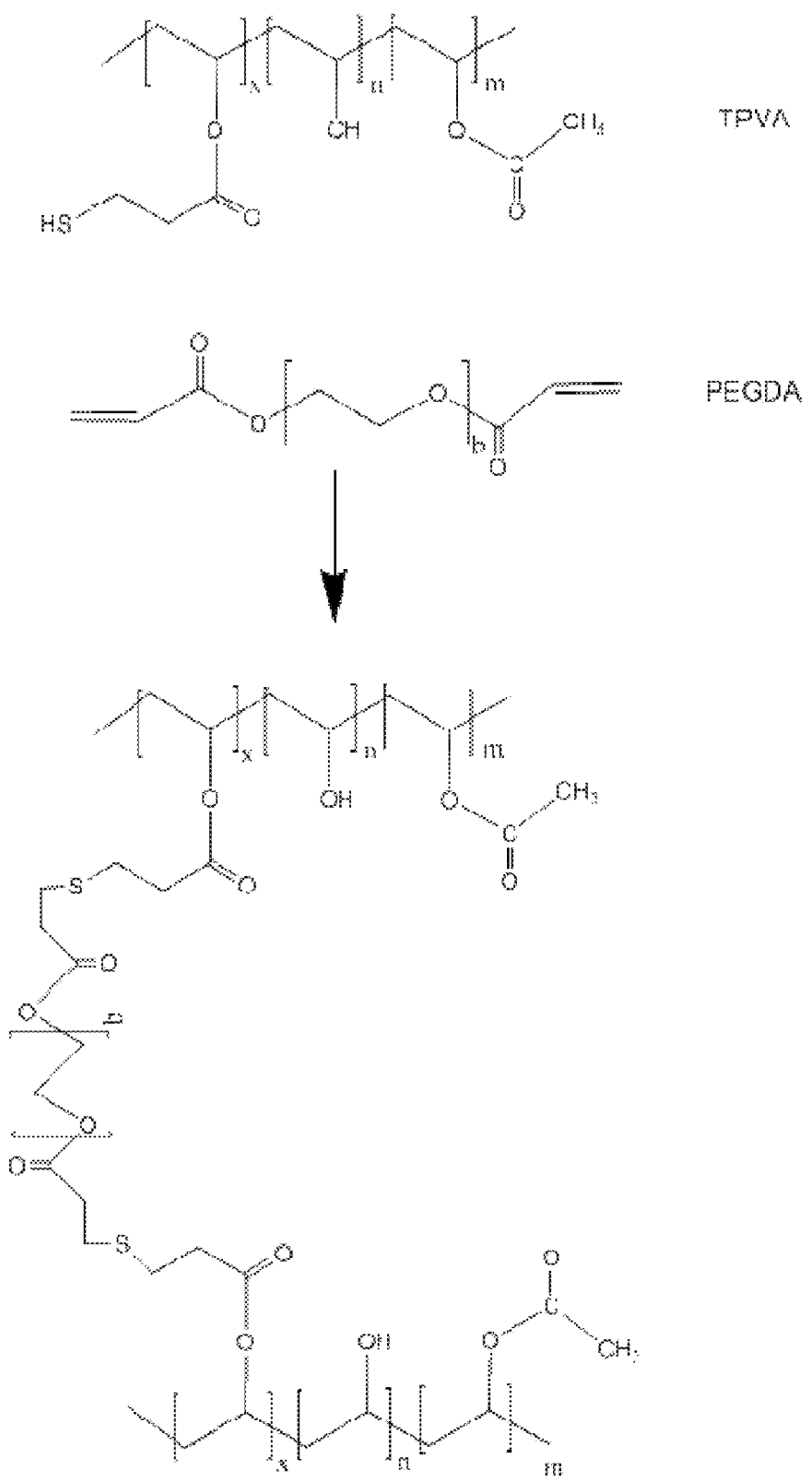
FIG. 3 illustrates a flow diagram of cross-link formation between the poly(ethylene glycol) and the thiolated poly(vinyl alcohol)

The molecular weight of the poly(ethylene glycol) may be varied, and in some cases one of the thiol-reactive groups may be replaced with other structures to form dangling chains, rather than crosslinks. In embodiments, the molecular weight (Mw) is less than 20,000, including all values and ranges from 200 to 20,000, such as 200 to 1,000, 1,000 to 10,000, etc. In addition, the degree of functionality may be varied, meaning that the poly(ethylene glycol) may be mono-functional, di-functional or multi-functional. The cross-links between the poly(ethylene glycol) and thiolated poly(vinyl alcohol) are formed as a result of thiol-ene addition, rendering sulfur-carbon covalent bonds linking polymer molecules, via Michael reactions as illustrated in FIG. 3. It is understood that while only one poly(ethylene glycol) crosslink between two poly(vinyl alcohol) chains are illustrated, more than one crosslink may be present between more than two poly(vinyl alcohol) chains). In addition, the polyethylene glycol may be linear, or branched, or any variation thereof.

In further embodiments, other crosslinkers, such as tocotrienol or lycopene could be tied to a poly(vinyl alcohol) polymer in a manner similar, wherein the tocotrienol or lycopene include thiol reactive groups, similar to the thiol reactive groups of the poly(ethylene glycol). The tocotrienol or lycopene then provide crosslinking between the thiolated poly(vinyl alcohol) chains. Therefore, crosslinkers may include not only poly(ethylene glycol) but also other compounds, which may be used in addition to or alternatively to the poly(ethylene glycol), that exhibit a molecular weight in the range of 200 to 20,000 and include thiol reactive groups. The thiol reactive groups polymerizing with the thiol containing functional groups of the thiolated poly(vinyl alcohol) to form a hydrogel.

In embodiments, aqueous solutions of both polymers are provided. The solutions of the thiolated poly(vinyl alcohol) and poly(ethylene glycol) are relatively low viscosity liquids. In embodiments, the thiolated poly(vinyl alcohol) and poly(ethylene glycol) solutions exhibit a viscosity in the range of 0.004 Pa*s to 0.5 Pa*s, including all values and ranges therein, such as 0.010 Pa*s to 0.05 Pa*s. For example, poly(ethylene glycol) diacrylate is present in solution at a concentration of 3 mg/mL to 300 mg/mL, including all values and ranges therein, and preferably in the range of 10 mg/mL to 50 mg/mL and more preferably at 30 mg/mL. The poly(ethylene glycol) diacrylate solution exhibits a viscosity in the range of 0.007 Pa*s to 0.5 Pa*s, including all values and ranges therein, and preferably in the range of 0.01 Pa*s to 0.05 Pa*s, and more preferably at 0.035 Pa*s. The thiolated poly(vinyl alcohol) is present in solution in a range of 10 mg/mL to 200 mg/mL, including all values and ranges therein, preferably in the range of 40 mg/mL to 80 mg/mL, and more preferably 60 mg/mL. Furthermore, the viscosity of the thiolated poly(vinyl alcohol) is in the range of 0.004 Pa*s to 0.2 Pa*s, including all values and ranges therein, preferably in the range of 0.010 Pa*s to 0.040 Pa*s and more preferably 0.020 Pa*s.

In embodiments of the above, the thiolated poly (vinyl alcohol) and poly(ethylene glycol) are delivered at a ratio of functional groups (mmol/mmol) in the range of 2:1 to 0.5:1, including all values and ranges therein, and preferably 1:1. Furthermore, once combined the combination of the thiolated poly(vinyl alcohol) and the poly (ethylene glycol) are present in solution in the range of 6 mg/mL to 250 mg/mL, including all values and ranges therein, and preferably 25 mg/mL to 65 mg/mL, and more preferably 45 mg/mL. The viscosity of the thiolated poly(vinyl alcohol) and the poly (ethylene glycol), prior to crosslinking and gelation, is in the range of 0.005 Pa*s to 0.35 Pa*s, including all values and ranges therein, such as in the range of 0.010 Pa*s to 0.040 Pa*s, and more preferably 0.028 Pa*s.

Thus, the polymer solutions are relatively easy to prepare and handle. As noted above, in embodiments, the thiolated poly(vinyl alcohol) and poly(ethylene glycol) cross-linking reactions proceed at temperatures in the range of 0° C. to 95° C., including all values and ranges therein, such as 20° C. to 45° C., upon mixing of the polymer components without UV irradiation or toxic initiators. In addition, crosslinking may be largely unaffected by pH or other solutes. In particular embodiments, crosslinking occurs under physiological conditions, wherein physiological conditions may be understood as conditions of the internal or external milieu that may occur in nature for an organism and include, for example, temperatures in the range of 20° C. to 40° C., a pH in the range of 6 to 8, and glucose concentrations in the range of 1 mM to 20 mM. Gelation may occur within 10 minutes to 30 minutes, including all values and ranges therein. No heat release or toxic by-products are formed during gelation and since the starting solutions are aqueous the hydrogel is partially or completely hydrated upon cure. The hydrogel may hydrate further depending on the osmotic load of the surrounding media.

The properties and gelation times of the in situ formed gels can be regulated by concentration of thiolated poly (vinyl alcohol) and poly(ethylene glycol), their ratio used for cross-linking and functionality (amount of thiol groups linked to poly(vinyl alcohol) and the amount of thiol reactive groups per poly(ethylene glycol) molecule). By changing thiolated poly(vinyl alcohol) to poly(ethylene glycol) ratio, one can also regulate the fraction of dangling poly (ethylene glycol) chains that can be used to improve hydrogel's surface properties. Furthermore, mixing a blend of mono-functional and bi-functional poly(ethylene glycol) crosslinkers, wherein the functionality is the thiol reactive groups will allow the tuning of the crosslinking versus hydrophilicity of the hydrogel. Control of the length of the mono-functional and bi-functional crosslinker or the size of the starting poly(vinyl alcohol), allows modification of mechanical properties, swelling, lubricity, morphology, and hydrophilicity as well as frictional and wear properties.

In addition to the above, the hydrogels are relatively hydrolyzable due to the presence of ester groups in the crosslinker and can therefore be considered degradable in vivo, wherein the hydrogels turn into liquid after approximately 5 weeks at a temperature in the range of 20° C. to 25° C., such as from 4 weeks to 10 weeks, including all values and ranges therein. In embodiments, the ester bonds remaining in the hydrogel may degrade at room temperature in solution, such as in a phosphate buffered saline solution. In embodiments, degradation may begin after a few days and the hydrogel may be almost fully degraded, that is they form soluble products and the hydrogel turns in to liquid at around five weeks at a temperature in the range of 20° C. to 25° C. The rate of degradation will depend on a number of parameters, including total crosslink density, number of ester linkages in the crosslinks and the specifics of the environment.

In addition, the hydrogels and the degradation products of the hydrogels are understood to be biocompatible, wherein the hydrogels and degradation products of the hydrogels do not have toxic or injurious effects on biological systems. Further, in the selection of appropriate molecular weight of the thiolated poly(vinyl alcohol) and containing poly(ethylene glycol) allows for relatively easy elimination by passing through kidneys.

Deliberate inclusion of degradable constituents would naturally allow tuning of the degradability and longevity of these materials in their chosen application. Examples of degradable constituents can be in the crosslinks, or elsewhere and can include, for example, any molecule or group that contains an ester bond (e.g. carbamate, amide, carbonate, lactic acid, glycolic acid, caprolactone or others). In particular embodiments, the degradable elements may be incorporated at an amount in the range of 1 to 6 per crosslinker. Similarly, as alluded to above, the incorporation of other functional groups into the hydrogel, such as though modification of the poly(vinyl alcohol) or poly(ethylene glycol) provide further degrees of tuning of the properties of the hydrogel.

As may be appreciated, only a fraction of the thiol groups of the thiolated poly(vinyl alcohol) are connected to the poly(ethylene glycol) cross-linker, wherein the linkers, i.e., the segments shared by the poly(ethylene glycol) and thiolated poly(vinyl alcohol), contain (—C—S—C—) units. It is contemplated that the degree of modification of the thiol groups of the thiolated poly(vinyl alcohol) is in the range 0.1 to 2.0% mol (~2.9-25% weight), leaving 1.0 to 10.0% mol available for other reactions. In one example, it is contemplated that 1% of thiol groups can be used for crosslinking reaction, leaving 1.0-9.0% mol for conjugation or other reactions. In embodiments, at least two thiol groups per molecule are required for crosslinking and conjugation, therefore the minimum molar percentage of thiol groups is determined by thiolated poly(vinyl alcohol) molecular weight.

As alluded to above, thiol groups, not used in cross-linking reactions, can be used for conjugation with drugs or for improving matrix surface properties. In embodiments, 1.0-9.0% mols of the thiol groups, including all values and ranges therein, can be used for conjugation with drugs, particularly where 1% is used for crosslinking. In addition, or alternatively, the non-crosslinked thiol groups may be utilized in binding to mucus, rendering the hydrogels mucoadhesive. In a method of employing the thiolated poly(vinyl alcohol)-poly(ethylene glycol) hydrogels, the thiolated polymers (sometimes referred to as thiomers) are mucoadhesive. Disulfide bonds are formed between the thiomers and the cysteine-rich subdomains of the mucus glycoproteins present in the mucus layer. Disulfide bonds are not influenced by ionic strength and pH. In contrast, other techniques that use end group functionalization of poly(vinyl alcohol) may allow either a crosslinking reaction to form a hydrogel, or crosslinking to mucus, but not both. Further, non-crosslinked thiol groups may bind with heavy metals. The chelation of the thiol groups to the heavy metals may allow for the hydrogels to act as a heavy metal filter. The non-crosslinked thiols groups may further bind with other thiols, noted above, present in the tissue allowing the hydrogels to adhere to the tissue.

In further embodiments, where it is not necessary or preferable to form the hydrogels under physiological conditions, freeze-thaw cycles may be employed to form the thiolated poly(vinyl alcohol) into hydrogels. In such embodiments, the poly(vinyl alcohol) is thiolated through the pathways described above, wherein a thiol containing functional group including thiol functionality and at least one hydroxyl-reactive group is coupled to poly(vinyl alcohol) in the presence of acid. In embodiments, non-thiolated poly(vinyl alcohol) may be used in combination with the thiolated poly(vinyl alcohol). When present in combination, the thiolated poly(vinyl alcohol) may be present in the range of 1% to 100% of the total poly(vinyl alcohol) content, including all values and ranges therein, and the non-thiolated poly(vinyl alcohol) may be present in the range of 99% to 0%, including all values and ranges therein such as 1% to 99%, of the total poly(vinyl alcohol) content. The non-thiolated portions of the PVA molecules will hydrogen bond together following understood processes to form a so-called cryogel composed of PVA with some thiol moieties capable of binding to thiol-reactive species either in the form of poly(ethylene glycol) as outlined above, or as a mucin or similar.

The thiolated poly(vinyl alcohol) may also be forced to form a physically crosslinked hydrogel with non-thiolated poly(vinyl alcohol) (if present) in water, or another aqueous based solution such as isotonic saline, at a concentration in the range of approximately 5% to 50% wt of the total weight of the solution approximately, including all values and ranges therein. It can also be solubilized in DMSO at similar levels. To solubilize the poly(vinyl alcohol) (either thiolated, non-thiolated, or a mixture thereof), the solution may be exposed to elevated temperatures, such as temperatures above 30° C. or greater, such as in the range of 30° C. to 95° C., including all values and ranges therein, at pressures in the range of 1 to 1.5 atm, including all values and ranges therein.

Poly(ethylene glycol) may then be added to the poly(vinyl alcohol) solution. In such embodiments, the polyethylene glycol may or may not include thiol-reactive end groups. The polyethylene glycol may be linear, branched, multi-armed or assembled into brushes. Equation 7 below illustrates an embodiment of PEG:

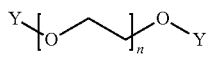

Eq. 7)

wherein each Y is individually selected from H or a thiol reactive end group including the above mentioned end groups and n is in the range of 200 to 20,000. In alternative or additional embodiments, the poly(ethylene glycol) may be a dendrimer. For example, the poly(ethylene glycol) may be a 4 to 32 hydroxyl dendron. In further alternative or additional embodiments, the poly(ethylene glycol) may be multi-armed. In such embodiments, the poly(ethylene glycol) may be, for example, a 4, 6 or 8 arm and hydroxy-terminated.

The poly(ethylene glycol) may be added directly to the poly(vinyl alcohol) solution or solubilized in an aqueous solution or DMSO before addition to the poly(vinyl alcohol) solution. When provided in solution prior to addition to poly(vinyl alcohol), the poly(ethylene glycol) is present in the range of 3 mg/mL to 300 mg/mL, including all values and ranges therein. After combination of the poly(vinyl alcohol) and poly(ethylene glycol) solutions into a mixture, the poly(vinyl alcohol) and poly(ethylene glycol) are present at a concentration in the range of 6 mg/mL to 250 mg/mL, including all values and ranges therein.

The poly(vinyl alcohol) solution, which may or may not include poly(ethylene glycol) is then exposed to one or more freeze thaw cycles, including from 2 to 6 freeze thaw cycles. The mixture may be poured into a mold or cast onto a surface, depending upon the end use of the hydrogel. Air bubbles may also be removed from the mixture by allowing the mixture to rest or placing the mixture under vacuum. The mixture is then exposed to a temperature in the range of −5° C. to −20° C., including all values and ranges therein, for a time period in the range of from 2 hours to 16 hours, including all values and ranges therein, freezing the mixture. After freezing, the mixture is exposed to a temperature in the range of 5° C. to 40° C., including all values and ranges therein, for a time period in the range of 2 hours to 16 hours, including all values and ranges therein, thawing the mixture. However, the temperature is maintained below the temperature which the poly(vinyl alcohol) solubilizes. As noted above, the mixture may be exposed to additional freeze-thaw cycles. The temperatures and exposure times in each cycle may be individually selected. The more freeze thaw cycles that occur, the higher the relative tensile strength and tensile stiffness of the hydrogel.

In yet further embodiments, the hydrogels are formed following the process described in U.S. Pat. No. 7,776,352, the teachings of which are incorporated by reference herein. In embodiments, the thiolated poly(vinyl alcohol) and optionally non-thiolated poly(vinyl alcohol) are dissolved or solubilized in a first solvent, which has a Flory interaction parameter that is insufficient to cause gelation, i.e., being a solvent that the energy of interaction between the poly(vinyl alcohol) and a solvent molecule adjacent to the polymer element exceeds the mean of the energies of interaction between the polymer-polymer and the solvent-solvent pairs. When provided together, the thiolated poly(vinyl alcohol) may be present in the range of 1% to 100% of the total poly(vinyl alcohol) content, including all values and ranges therein, and the non-thiolated poly(vinyl alcohol) may be present in the range of 99% to 0%, including all values and ranges therein such as 1% to 99%, of the total poly(vinyl alcohol) content.

The Flory interaction parameter ($\chi$) is understood as a dimensionless number characterizing polymer interaction energy taken as: $z\Delta\epsilon/kT$, wherein $\Delta\epsilon$ is the enthalpy of interaction of a polymer segment with solvent, k is Boltzmann's constant and T is the absolute temperature and is dependent on, for example, temperature, concentration and pressure. The Flory interaction parameter of the poly(vinyl alcohol) in the solvent may be below 0.5 and examples of the first solvent include deionized water, dimethyl sulfoxide, an aqueous solution of a $C_1$ to $C_6$ alcohol, and mixtures thereof.

The poly(vinyl alcohol) is presented in the first solution at a concentration in the range of 1% by weight to 50% by weight of the total weight of the solution, including all values and ranges therein. The poly(vinyl alcohol) is solubilized in the first solution by raising the temperature of the solution in the range of 10° C. to 90° C., including all values and ranges therein, for a time period in the range of 10 minutes to 2 hours. The poly(vinyl alcohol) becomes dissolved in the solution.

The poly(vinyl alcohol) solution is then contacted with a second solvent that raises the Flory interaction parameter sufficiently to enable gelation, such as in the range of 0.5 or greater and up to 1.0. The second solvent may include common salt, non-reactive polyethylene glycol, chondroitin sulfate etc. The polyethylene glycol may be linear, branched, multi-armed or assembled in brushes. In such embodiments, the polyethylene glycol may or may not include thiol-reactive end groups, as represented in Equation 7 reproduced again below:

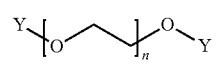

Eq. 7)

wherein each Y is individually selected from H or a thiol reactive end group including the above mentioned end groups and n is in the range of 200 to 20,000. While gelation may begin irrespective of temperature, in embodiments, the temperature of the solution may be lowered to a temperature in the range of 10° C. to 60° C., including all values and ranges therein, either prior to or after contacting the solution with the poly(ethylene glycol). This temperature reduction results in the physical gelation of the polymers. The poly(ethylene glycol) is present in the first solution at a concentration in the range of 15 to 50% wt, including all values and ranges therein. Contacting of the thiolated poly(vinyl alcohol) and optional non-thiolated poly(vinyl alcohol) with the poly(ethylene glycol) results in the formation of the hydrogel. The non-functionalized PEG acts as an "inert" gellant and will diffuse out if the hydrogel is placed in a suitable environment. The functional PEG can be added at the same time as the non-functional PEG to both react with the thiolated PVA and drive the phase separation, or it can be diffused in after the physical gelation to provide subsequent reaction to the thiolated PEG after the phase separation structure has been formed.

It is contemplated that the hydrogels provided above may provide a relatively more porous structures upon degradation of the thiolated poly(vinyl alcohol) leaving the non-thiolated PVA. This porosity may be controlled, in part, by the proportions of thiolated poly(vinyl alcohol) and non-thiolated poly(vinyl alcohol) present in the composition. Furthermore, the presence of any degradable constituents may further tune the porosity of the hydrogels. The presence of the thiolated PVA will also render this physically gelled hydrogel mucoadhesive.

As alluded to above, the hydrogels are employed in a variety of applications. Some of these applications including biologically related applications, wherein the thiolated poly(vinyl alcohol)-poly(ethylene glycol) systems may be delivered to various sites of a subject, such as vertebrates, mammals or preferably humans, through injection of the hydrogels into defects or implantation of manufactured hydrogels into defects sites. The hydrogels may be used as a temporary tissue bulking agent, or as load-bearing constructs in static or articulating joints. In addition, or alternatively, the hydrogels may be impregnated or coated with one or more pharmaceutical compositions. Also in addition to, or alternatively to the above, the hydrogels may be a cell or drug carrier, wherein as alluded to above, the poly(vinyl alcohol) or PEG may be functionalized to bond, covalently, with various pharmaceutical compositions. Pharmaceutical compositions may be understood as molecular entities and compositions that do not produce an adverse, allergic or other untoward reaction when administered to a subject, such as, for example, a human in an effective amount. These compositions may aid in the treatment of a subject in need of such treatment. "Treatment" or "treating" is understood herein to identify, diagnose, detect, target, ameliorate, reduce, minimize or limit the extent of the disease, condition or associative disorder.

Stated another way, the pharmaceutical compositions may be generally safe, non-toxic, and neither biologically nor otherwise undesirable. It should be understood however, that aberrations are plausible, where a relatively statistically insignificant portion of the population may be adversely affected by a given composition. The preparation of a pharmaceutical composition is generally known to those of skill in the art. Moreover, for animal (e.g., human) administration, it is preferred that the preparations meet sterility, pyrogenicity, general safety, and purity standards as required by the FDA Office of Biological Standards.

An "effective amount" of a pharmaceutical composition is, generally, defined as that amount sufficient to identify, diagnose, detect, target, ameliorate, reduce, minimize or limit the extent of the disease or condition. More or less rigorous definitions may apply, including elimination, eradication, or cure of a disease or condition. Less rigorous definitions may apply as well, including producing reproducible and evaluable images. As understood in the art, the effective amount of the hydrogels described herein may vary based on the component, the nature and severity of the condition to be treated, the age and condition of the subject to be treated, and other factors.

A "pharmaceutically acceptable carrier" may be used to facilitate administration of the hydrogel precursors parenterally, including for example, infusion, injection or implantation. "Pharmaceutically acceptable carriers" include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

The actual amount of the hydrogels administered to a subject can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

Accordingly, in embodiments, the hydrogels are formed in situ under physiological conditions. These gels could be used in any application where a highly hydrated space-filling hydrogel may be advantageous, such as tissue bulking application for cosmetic surgery, urinary or renal incontinence and reflux. The material would also be useful in tissue biopsy markers, or any other application where tissue is excised and replaced by an injectable alternative. Due to its low toxicity profile, the material may also act as a scaffold for active cells and could find use in cartilage repair. Accordingly, the present application is directed to methods of delivering the hydrogel precursor compositions to a subject in need thereof. Once in place, the hydrogels are formed. The cross-linking does not require initiators or a UV source that can produce free radicals. During cross-linking, no by-products are formed or nor is heat released. As may be appreciated, the mild reaction conditions and lack of requirement of light initiation during hydrogel formation make thiolated poly(vinyl alcohol)-poly(ethylene glycol) systems especially suitable in delivery of environmentally sensitive molecules such as proteins and peptides and encapsulation and delivery of cells.

In further embodiments the hydrogels may be used as coatings on medical devices including surgical instruments, sensors, detectors, optical analysis probes (in vivo or industrial). Hydrogel or hydrogel precursors may be applied to the devices in a number of ways, such as dip coating, spray coating, etc. The devices may be formed from polymer materials that are functionalized with hydroxyl or thiol reactive moieties, providing crosslinking between the hydrogels and the devices. Such devices may include sensors, detectors, surgical instruments, optical analysis probes, etc.

The thiolated poly(ethylene glycol)-polyvinyl alcohol hydrogels discussed herein allow for the deployment of hydrogels without toxic initiators, UV radiation, organic solvents or elevated temperatures. The components exhibit a relatively low viscosity that allows the injection and formation of the hydrogel in situ. Furthermore, the gelation process is suitable for in vivo applications.

EXAMPLES

Example 1: Functionalization of PVA

Thiolated poly(vinyl alcohol) was synthesized by the esterification of poly(vinyl alcohol), 98-99% hydrolyzed, Mw 31-50 kDa: Sigma-Aldrich, Catalog #363138-500G, Batch #027028 LD with 3-mercaptopropionic acid: Sigma-Aldrich, Catalog #M5801-100G in the presence of hydrochloric acid. Specifically, to 5.0 g of poly(vinyl alcohol) dissolved in 30 mL of water at 80° C. was added dropwise a mixture of 3-mercaptopropionic acid (6.0 g) and hydrochloric acid (1.0 ml, 7N). After refluxing at 80° C. for 15 hours, the mixture was poured into 500.00 mL of methanol, the white precipitate was collected and washed several times with methanol and dried under vacuum at room temperature.

Figure 4:
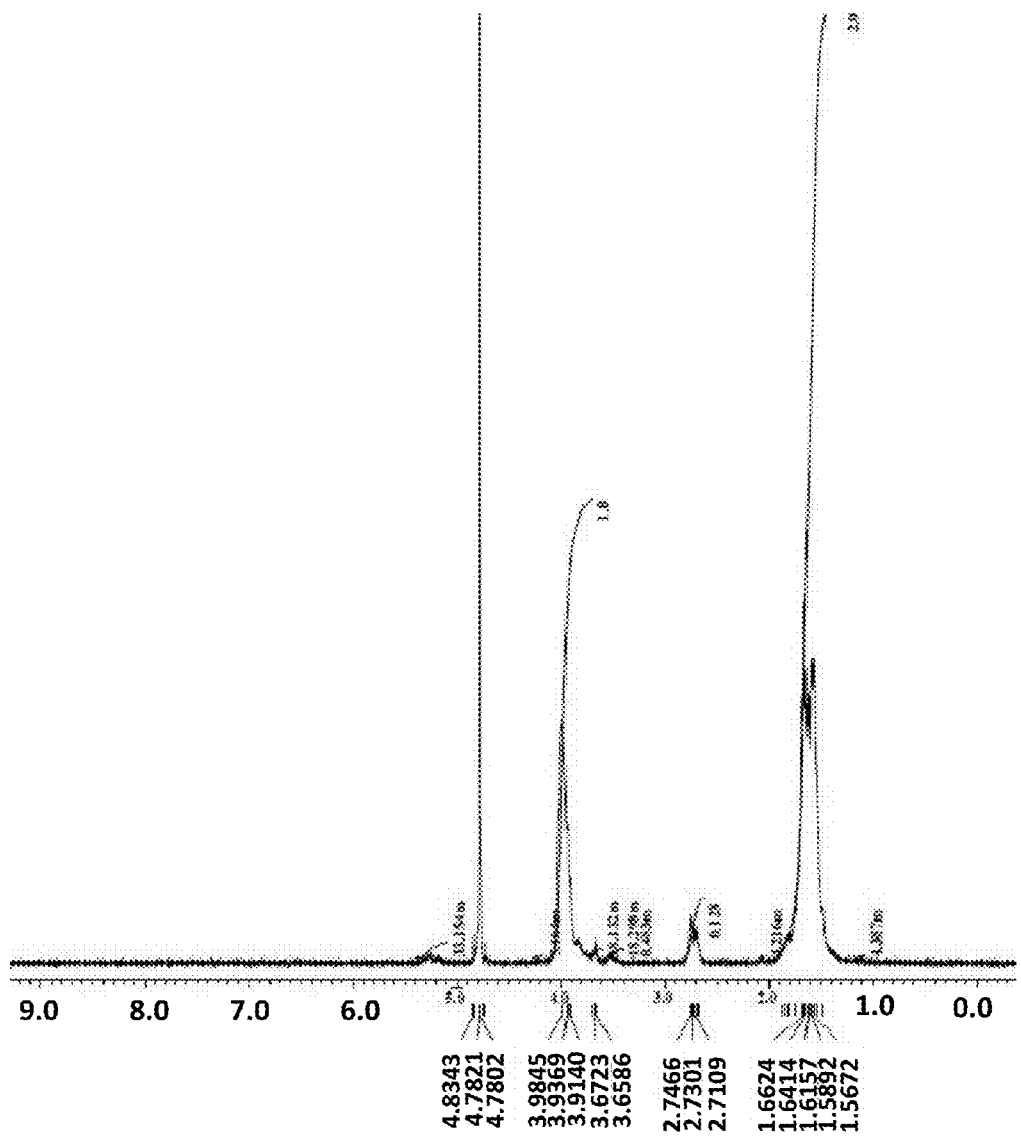
FIG. 4 illustrates a representative $H^1$ NMR spectrum at 300 MHz of thiolated poly(vinyl alcohol)

Representative $^1$H NMR spectrum at 300 MHz of the thiolated poly(vinyl alcohol) (TPVA) is shown in FIG. 4. The multiplet at δ around 2.7-2.8 ppm corresponds to methylene protons of 3-mercaptopropionic ester fragment, and allows estimation of a percent thiolation at around 3% for the sample in FIG. 4.

Example 2: Gelation of Thiolated Poly(Vinyl Alcohol)

Thiolated poly(vinyl alcohol) gels were prepared by mixing aqueous solution of the thiolated poly(vinyl alcohol) as prepared in example 1 with a solution of poly (ethylene glycol) acrylate (PEGDA), Mw 3400 Da: Sunbio, Lot #C2AC-003-09137, in phosphate buffered saline solution (1×PBS). TPVA (3% thiol groups) was dissolved in water by heating solution at 50° C. for complete dissolution of solids to obtain concentrations 2-6% (w/v). PEGDA was dissolved in the 1×PBS at room temperature to concentrations 1-3% (w/v). The concentrations of polymers have been selected to achieve equivalent molar concentrations between thiol groups of thiolated poly(vinyl alcohol) and diene groups of PEGDA. The solutions were mixed using magnetic stir bar or hand shaking. Gel formation occurred within minutes to hours depending on polymer concentration and temperature of gelation.

Figure 5:
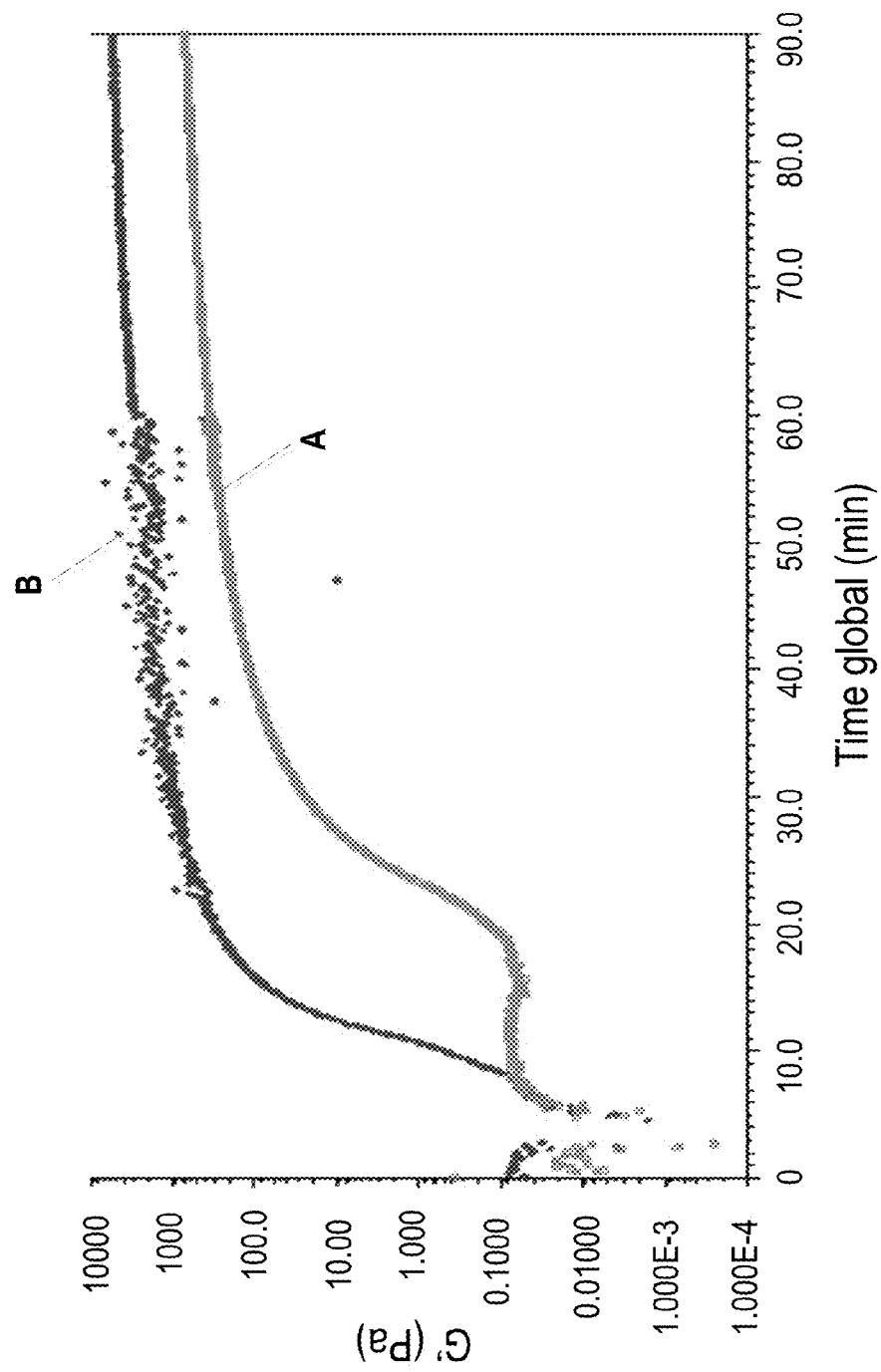
FIG. 5 illustrates a time sweep of gelation kinetics for a 3% and 4.5% polymer solution (including both TPVA and PEGDA) at 25° C. and a frequency of 1 Hz.

An example of the in situ kinetics of gel formation is shown in FIG. 5. In this example, 0.5 ml of thiolated poly(vinyl alcohol) (6% w/v) in water was mixed with 0.5 ml of PEGDA (3% w/v) in 1×PBS and placed in rheometer's plate set at 25° C. to acquire time sweeps at a frequency of 1 Hz. The kinetics of gelation was monitored at polymer concentrations 3% and 4.5% (illustrated in FIG. 5, "A" is the 3% solution and "B" is the 4.5% solution). The system was also monitored at temperatures 37° C. (figure not shown). The data for all of these runs are summarized in Table 1.

TABLE 1

Gelation times and Dynamic modulus determined from time sweeps at a frequency of 1 Hz.

| Polymer* concentration, weight % | Temperature, ° C. | | | | | |
|---|---|---|---|---|---|---|
| | 25° C. | | | 37° C. | | |
| | Gelation time**, min | $G'_{equil}$, Pa | $G''_{equil}$, Pa | Gelation time, min | $G'_{equil}$, Pa | $G''_{equil}$, Pa |
| 3.0 | 23.3 | 803 | 5 | 4.2 | 3607 | 480 |
| 4.5 | 9.2 | 6440 | 133 | 3 | 9857 | 281 |

It is noted that *polymer concentration is presented as a sum of TPVA and PEGDA concentrations; **gelation time is determined at cross-over point between G' and G"; and $G'_{equil}$ and $G''_{equil}$ are values obtained after 2 hours from the start of gelation.

Example 3: Swelling and Degradation of Thiolated Poly(Vinyl Alcohol)/Poly(Ethylene Glycol) Diacrylate Hydrogels Thiolated poly(vinyl alcohol)-PEGDA hydrogels in triplicates were prepared by mixing 100 μl thiolated poly(vinyl alcohol) as prepared in example 1 (6% w/v) in water with 100 μl PEGDA (3% w/v) in 1×PBS (phosphate buffered saline) at room temperature. The gelation occurred within 17-19 minutes. The gels were weighed, and this weight was designated as initial weight (Wo). To each of the gels was added 1.0 ml of 1×PBS. After predetermined time points (0 hours, 1 hour, 6 hours and 14 hours), 1×PBS was decanted, gels were withdrawn from vials, and water from gel's surfaces was removed with Kimwipes. The gels were weighed again to obtain a post swelling weight (W), and swelling percentage was calculated as follows.

$$(W-Wo)/Wo \quad \text{Eq. 2}$$

Figure 6:
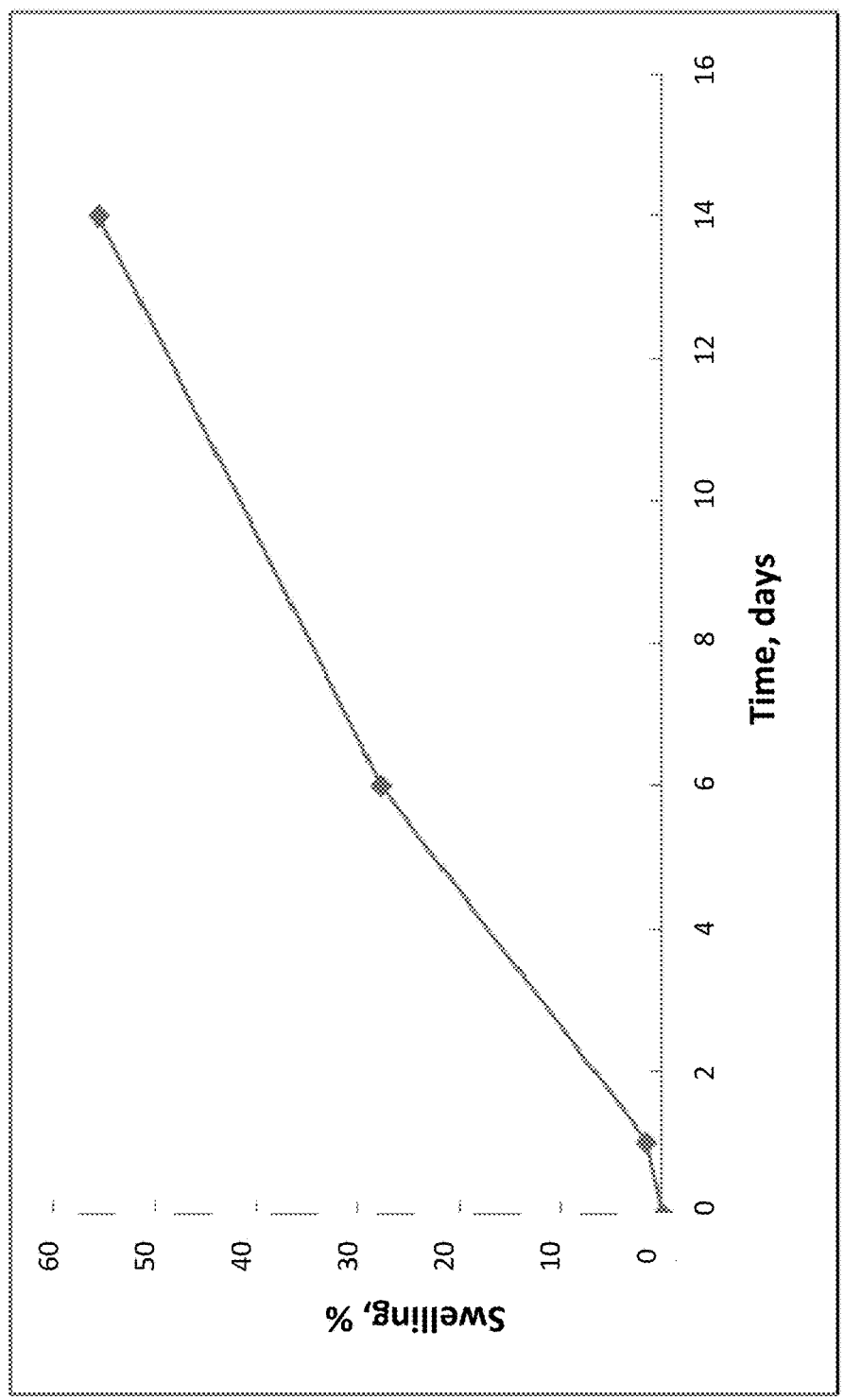
FIG. 6 illustrates representative swelling kinetic data.
Figure 7:
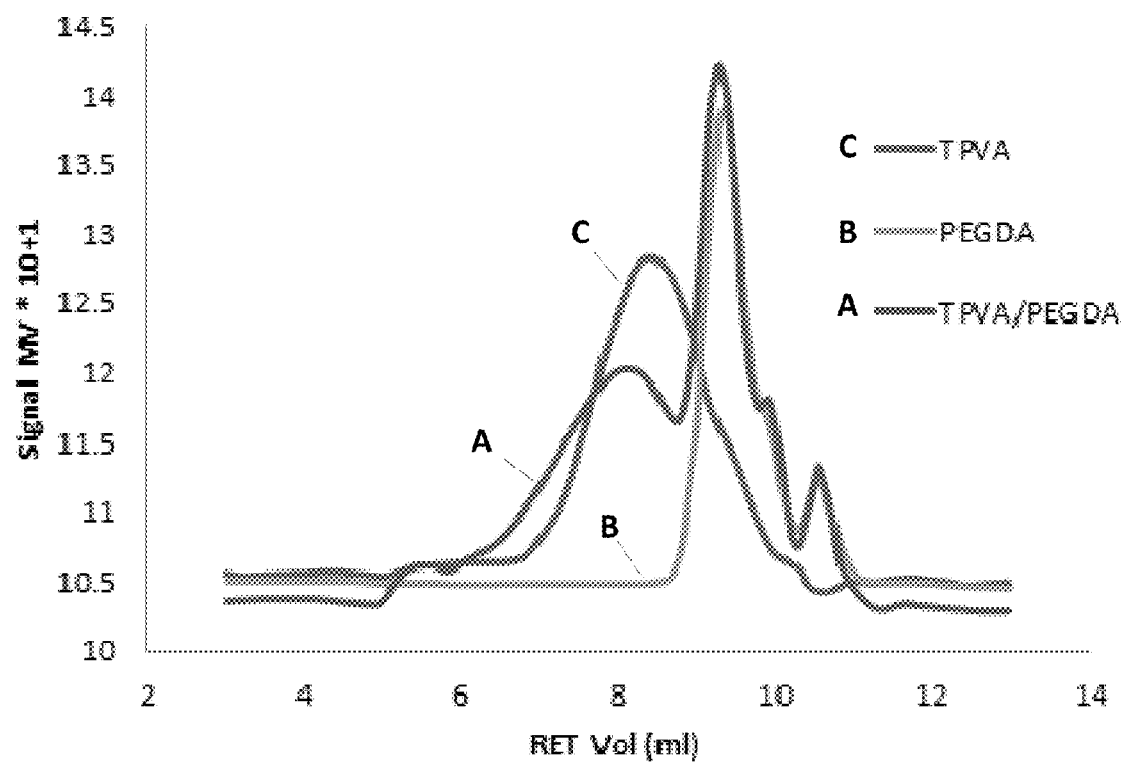
FIG. 7 illustrates liquid degradation products of the thiolated poly(vinyl alcohol)-poly(ethylene glycol) diacrylate.
Figure 8:
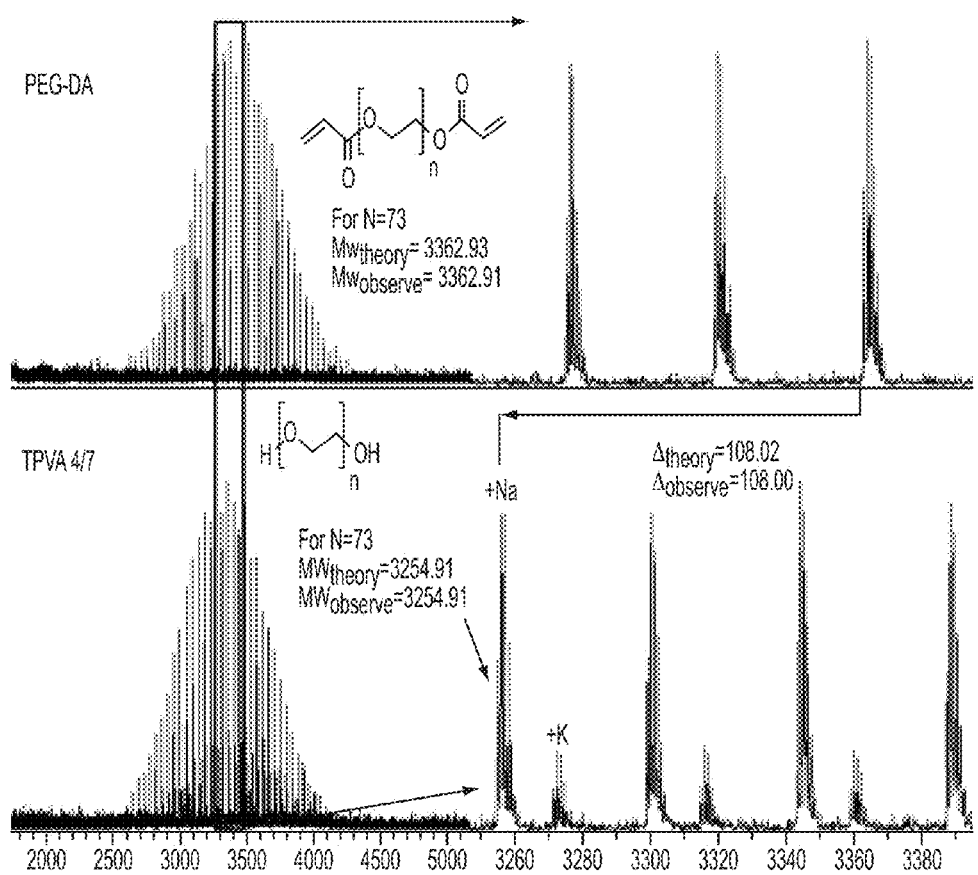
FIG. 8: MALDI-TOF MS Analysis of PEGDA used for synthesis of TPVA hydrogels (upper mass spectrum) and degradation product PEGOH (lower mass spectrum)

The new portion of 1×PBS was added to the gel for subsequent measurements. FIG. 6 provides data on the formulation's swelling kinetics. After 18 days from the start of the swelling test the hydrogels began disintegrating in to small pieces upon gentle shaking. After five weeks gels completely degraded and formed homogeneous transparent solutions in 1×PBS. FIG. 7 shows liquid degradation products of thiolated poly(vinyl alcohol)-poly(ethylene glycol) diacrylate hydrogel obtained by GPC analysis. The peaks of hydrogel degradation products (A) correspond to molecular weights of poly(ethylene glycol) diacrylate (B) at 9.3 mL retention volume and thiolated poly(vinyl alcohol) (C) at 8.3 mL retention volume, compounds used for hydrogel synthesis, indicating them as the main degradation products. FIG. 8 shows analysis of these degradation products by MALDI (matrix-assisted laser desorption/ionization). Mass spectrum of PEGDA precursor compound used for the synthesis of TPVA hydrogels is shown on the upper plot of FIG. 8. Its molecular weight Mn=3363 corresponds to 74 ethylene glycol repeat units. Molecular weight of degradation product Mn=3255, shown in lower plot of FIG. 8, corresponds to ester hydrolysis of precursor PEGDA with Mn=3363 and was identified as PEG with end capped hydroxyl groups (PEGOH). It should be noted that there is an additional peak at "M+16," which is presumed to be ionization from potassium rather than sodium that was originated due to potassium chloride in 1×PBS. The presence of PEGOH confirms that degradation occurs through ester bond hydrolysis of precursor PEGDA incorporated into TPVA hydrogel with the formation of biocompatible PEG and PVA as main products.

Example 4: Mucoadhesive Properties of Thiolated Poly(Vinyl Alcohol)

Figure 9:
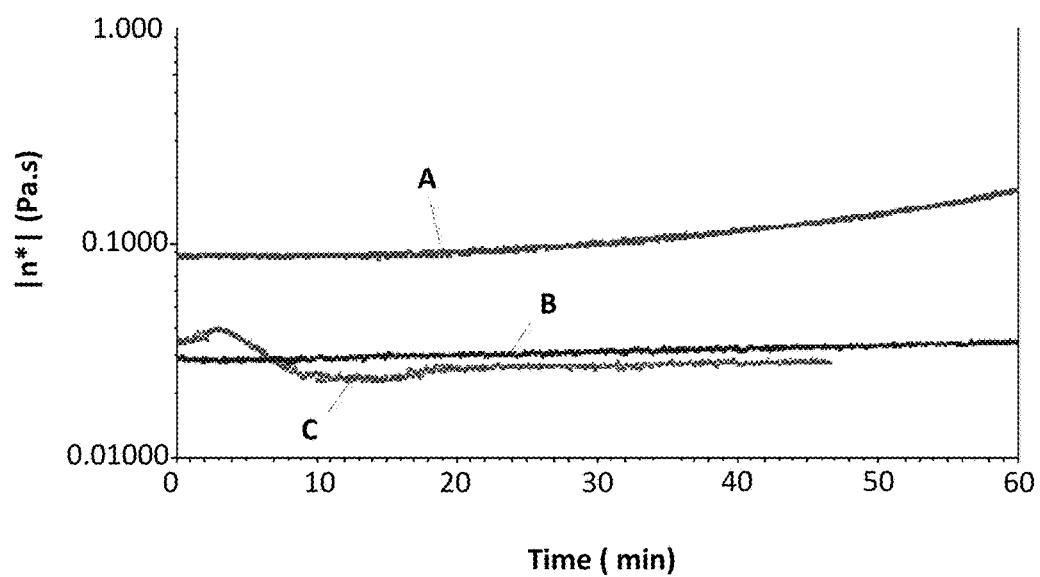
FIG. 9 illustrates representative viscosities of thiolated poly(vinyl alcohol), mucin and a thiolated poly(vinyl alcohol) and mucin mixture.

Mucoadhesive properties of thiolated poly(vinyl alcohol) were assessed by viscosity measurements in the presence of mucin. The viscosity of thiolated poly(vinyl alcohol) at 30 mg/mL and mucin at 40 mg/mL was measured at 25° C. after incubation for 20 minutes and used as the controls. The viscosity of thiolated poly(vinyl alcohol) after mixing with mucin was measured under the same conditions and compared with the viscosities of individual thiolated poly(vinyl alcohol) and mucin, which are illustrated in FIG. 9. The complex viscosity of thiolated poly(vinyl alcohol)/mucin mixture (0.087 Pa s) was found to be more than two times exceeded that of individual thiolated poly(vinyl alcohol) (0.03 Pa s) and mucin (0.03 Pa s). It also increased over 1 hour period test time, indicating that the reactions have taken place between the two components.

Accordingly, an aspect of the present disclosure relates to a method of forming thiolated poly(vinyl alcohol) hydrogels. The method includes reacting, in the presence of an acid, compounds each including a thiol functional group and a hydroxyl reactive group with one or more hydroxyl groups of poly(vinyl alcohol) via the hydroxyl reactive group, thereby forming thiolated poly(vinyl alcohol). The method also includes reacting the thiol functional group of the compounds with a thiol reactive group of a crosslinker, thereby forming a hydrogel.

A further aspect of the present application relates to a method of forming a hydrogel via one or more freeze thaw cycles. The method includes reacting, in the presence of an acid, compounds each including a thiol functional group and a hydroxyl reactive group with one or more hydroxyl groups of poly(vinyl alcohol) via the hydroxyl reactive group, thereby forming thiolated poly(vinyl alcohol). The method further includes solubilizing poly(vinyl alcohol) and the thiolated poly(vinyl alcohol) to form a solution and adding poly(ethylene glycol) to the solution. The solution may be exposed to one or more freeze thaw cycles forming the hydrogel.

Yet another aspect of the method relates to a method of forming a hydrogel by altering the Flory interaction parameter of the solvents to enable gelation. The method includes reacting, in the presence of an acid, compounds each including a thiol functional group and a hydroxyl reactive group with one or more hydroxyl groups of poly(vinyl alcohol) via the hydroxyl reactive group, thereby forming thiolated poly (vinyl alcohol). The method further includes solubilizing the thiolated poly(vinyl alcohol) in a first solvent forming a first solution, wherein the first solvent has a Flory interaction parameter insufficient to cause gelation of the thiolated poly(vinyl alcohol). The first solution is contacted with a second solution wherein the second solvent increases the Flory interaction parameter to enable gelation and forming the hydrogel.

The foregoing description of several methods and embodiments has been presented for purposes of illustration. It is not intended to be exhaustive or to limit to the precise steps and/or forms disclosed, and obviously many modifications and variations are possible in light of the above teaching.

What is claimed is:

1. A method of forming thiolated poly(vinyl alcohol) hydrogels, comprising:
    reacting, in the presence of an acid, compounds each including a thiol functional group and a hydroxyl reactive group with one or more hydroxyl groups of poly(vinyl alcohol) via said hydroxyl reactive group, thereby forming thiolated poly(vinyl alcohol), wherein said compounds are randomly distributed along the poly(vinyl alcohol); and
    reacting said thiol functional group of said compounds with a thiol reactive group of a crosslinker, wherein said thiolated poly(vinyl alcohol) and said crosslinker are provided in aqueous solutions, thereby forming a hydrogel without UV radiation, wherein said crosslinker is poly(ethylene glycol) exhibiting the following formula

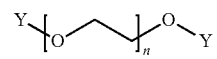

wherein each Y is individually selected from a thiol reactive group and n is in the range of 200 to 20,000, wherein said thiol reactive groups Y are selected from the groups consisting of acrylates, methacrylates, maleimide, haloacetyl, pyridyldithiol and N-hydroxysuccinimide.

2. The method of claim 1, wherein said thiol containing compounds exhibit the following formula:

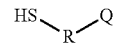

wherein R includes an alkane, iso-alkane, unsaturated ether, or ester group, and includes from 1 to 20 carbons and Q is a hydroxyl reactive group that includes acids, acyl halogenates, acid anhydrides and esters.

3. The method of claim 1, wherein said thiol containing compounds comprises 3-mercaptopropionic acid.

4. The method of claim 1, wherein said acid is selected from the group consisting of: hydrochloric acid, sulfuric acid and phosphoric acid.

5. The method of claim 1, wherein reacting said hydroxyl reactive groups of said compounds with said hydroxyl groups of said poly(vinyl alcohol) is performed at a temperature in the range of 40° C. to 95° C.

6. The method of claim 1, wherein said thiolated poly (vinyl alcohol) exhibits the following formula:

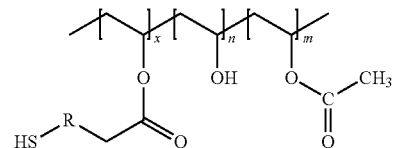

wherein R includes 1 to 20 carbons, x is in the range of 0.1-10%, n is in the range of 80-99.9% and m is in the range of 0.1-20%, wherein % x, n and m is the proportion of the total number of repeat units of said thiolated poly(vinyl alcohol).

7. The method of claim 1, wherein said compounds include amino acids.

8. The method of claim 1, wherein said crosslinker is a poly(ethylene glycol) diacrylate exhibiting the following formula:

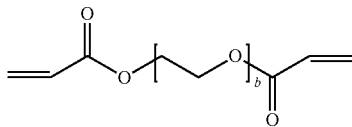

wherein b is in the range of 200 to 20,000.

9. The method of claim 1, wherein reacting said thiolated poly(vinyl alcohol) with a crosslinker is performed at a temperature in the range of 20° C. to 40° C.

10. The method of claim 1, further comprising binding said hydrogels with a heavy metal.

11. The method of claim 1, further comprising binding said hydrogels with mucins.

12. The method of claim 1, further comprising binding said hydrogels to thiols present in biological tissue.

13. The method of claim 1, wherein said thiol functional groups are present at a ratio of 0.1 mmol per mmol of poly(vinyl alcohol) to 10.0 mmol per mmol of poly(vinyl alcohol).

14. The method of claim 1, wherein said thiol functional groups with a thiol reactive groups of said crosslinker are reacted at a temperature in the range of 0° C. to 95° C.

15. The method of claim 1, wherein said thiolated poly(vinyl alcohol) and said poly(ethylene glycol) are delivered individually to a treatment site and combined in situ.

16. The method of claim 1, wherein said poly(vinyl alcohol) exhibits a molecular weight (Mw) in the range of 2 kDa to 1,000,000 kDa.

17. A method of forming a hydrogel, comprising:
reacting, in the presence of an acid, compounds each including a thiol functional group and a hydroxyl reactive group with one or more hydroxyl groups of poly(vinyl alcohol) via said hydroxyl reactive group, thereby forming thiolated poly(vinyl alcohol), wherein said compounds are randomly distributed on said thiolated-poly(vinyl alcohol);
solubilizing poly(vinyl alcohol) and said thiolated poly(vinyl alcohol) in water or an aqueous based solvent to form a solution;
adding poly(ethylene glycol) to said solution, wherein said poly(ethylene glycol) exhibits the following formula

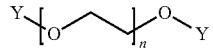

wherein each Y is individually selected from a thiol reactive group and n is in the range of 200 to 20,000, wherein said thiol reactive groups Y are selected from the groups consisting of acrylates, methacrylates, maleimide, haloacetyl, pyridyldithiol and N-hydroxysuccinimide; and
exposing said solution to one or more freeze thaw cycles and forming said hydrogel.

18. A method of forming a hydrogel, comprising:
reacting, in the presence of an acid, compounds each including a thiol functional group and a hydroxyl reactive group with one or more hydroxyl groups of poly(vinyl alcohol) via said hydroxyl reactive group, thereby forming thiolated poly(vinyl alcohol), wherein said compounds are randomly distributed on said thiolated-poly(vinyl alcohol);
solubilizing said thiolated poly(vinyl alcohol) in a first solvent forming a first solution, wherein said first solvent includes water and has a Flory interaction parameter insufficient to cause gelation of the thiolated poly(vinyl alcohol); and
contacting said first solution with a second solvent wherein said second solvent increases said Flory interaction parameter to enable gelation and forming said hydrogel, wherein said second solvent includes poly(ethylene glycol) exhibits the following formula

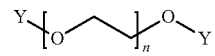

wherein each Y is individually selected from a thiol reactive group and n is in the range of 200 to 20,000, wherein said thiol reactive groups Y are selected from the groups consisting of acrylates, methacrylates, maleimide, haloacetyl, pyridyldithiol and N-hydroxysuccinimide.

19. A method of forming thiolated poly(vinyl alcohol) hydrogels, comprising:
reacting, in the presence of an acid, compounds each including a thiol functional group and a hydroxyl reactive group with one or more hydroxyl groups of poly(vinyl alcohol) via said hydroxyl reactive group, thereby forming thiolated poly(vinyl alcohol); and
reacting without UV radiation said thiol functional group of said compounds with a thiol reactive group of a crosslinker, thereby forming a hydrogel, wherein said crosslinker is tocotrienol or lycopene.

20. The method of claim 19, wherein said thiol containing compounds exhibit the following formula:

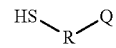

wherein R includes an alkane, iso-alkane, unsaturated ether, or ester group, and includes from 1 to 20 carbons and Q is a hydroxyl reactive group that includes acids, acyl halogenates, acid anhydrides and esters.

21. The method of claim 19, wherein said thiol containing compound comprises 3-mercaptopropionic acid.

22. The method of claim 19, wherein said acid is selected from the group consisting of: hydrochloric acid, sulfuric acid and phosphoric acid.

23. The method of claim 19, wherein reacting said hydroxyl reactive groups of said compounds with said hydroxyl groups of said poly(vinyl alcohol) is performed at a temperature in the range of 40° C. to 95° C.

24. The method of claim 19, wherein said thiolated poly(vinyl alcohol) exhibits the following formula:

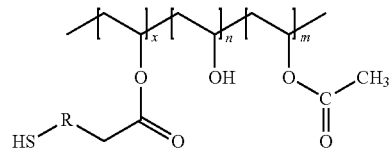

wherein R includes 1 to 20 carbons, x is in the range of 0.1-10%, n is in the range of 80-99.9% and m is in the range of 0.1-20%, wherein % x, n and m is the proportion of the total number of repeat units of said thiolated poly(vinyl alcohol).

25. The method of claim 19, wherein said compounds include amino acids.

26. The method of claim 19, wherein reacting said thiolated poly(vinyl alcohol) with said crosslinker is performed at a temperature in the range of 20° C. to 40° C.

27. The method of claim 19, further comprising binding said hydrogels with a heavy metal.

28. The method of claim 19, further comprising binding said hydrogels with mucins.

29. The method of claim 19, further comprising binding said hydrogels to thiols present in biological tissue.

30. The method of claim 19, wherein said thiol functional groups are present at a ratio of 0.1 mmol per mmol of poly(vinyl alcohol) to 10.0 mmol per mmol of poly(vinyl alcohol).

31. The method of claim 19, wherein said thiol functional groups are reacted with said thiol reactive groups of said crosslinker at a temperature in the range of 0° C. to 95° C.

32. The method of claim 19, wherein said poly(vinyl alcohol) exhibits a molecular weight (Mw) in the range of 2 kDa to 1,000,000 kDa.

* * * * *